United States Patent [19]

Huey-Long

[11] Patent Number: 4,942,251

[45] Date of Patent: Jul. 17, 1990

[54] PROCESS FOR PRODUCING α-ANTHRAQUINONESULFONIC ACIDS AND RECOVERING THE CATALYST USED THEREIN

[75] Inventor: Kou Huey-Long, Taipei, Taiwan

[73] Assignee: China Technical Consultants, Inc., Taiwan

[21] Appl. No.: 144,505

[22] Filed: Jan. 15, 1988

[51] Int. Cl.⁵ .............................. C07C 143/36
[52] U.S. Cl. .................................... 552/234
[58] Field of Search ................ 260/370; 552/234

[56] References Cited

U.S. PATENT DOCUMENTS 3,763,191  10/1973  Schmitz et al. ............... 260/370
3,792,065   2/1974  Hiller et al. .................. 260/370

FOREIGN PATENT DOCUMENTS 2712577  11/1977  Fed. Rep. of Germany ...... 260/370

OTHER PUBLICATIONS

"Anthraquinone Derivatives", vol. 2, pp. 729–733.
"Palladium–Catalyzed α–Monosulfonation of Anthraquinone by Sulfur Trioxide in Liquid Sulfur Dioxide", by Y. Kawabata et al., Nat'l Chemical Laboratory for Industry, 1980, pp. 322–325.

Primary Examiner—Richard L. Raymond
Assistant Examiner—Raymond Covington
Attorney, Agent, or Firm—Ostrolenk, Faber, Gerb & Soffen

[57] ABSTRACT

The present invention concern a process for producing α-anthraquinonesulfonic acids in the presence of a metal catalyst in oleum and recovering the metal catalyst which is solubilized in the resulting sulfonation mixture. A porous carrier is introduced into the resulting sulfonation mixture which is subsequently treated with a reducing agent thereby depositing the metal catalyst on the porous carrier.

17 Claims, No Drawings

PROCESS FOR PRODUCING α-ANTHRAQUINONESULFONIC ACIDS AND RECOVERING THE CATALYST USED THEREIN

TECHNICAL FIELD OF THE INVENTION

The present invention relates to a process for producing α-anthraquinonesulfonic acids by sulfonating anthraquinone in oleum and recovering the catalyst which is solubilized in the resulting sultonating mixture.

BACKGROUND OF THE INVENTION

In the process for the production of α-anthraquinonesulfonic acids by sulfonating anthraquinone in solvent, a metal type catalyst is required. Different catalysts and solvents have been disclosed in the past in order to accomplish the sulfonation reaction with a high conversion ratio and α-selectivity, and methods for recovering the catalyst also have been discussed. However, a process which has a high conversion ratio, α-selectivity, and in which the catalyst recovered therefrom retains the same activity has not been disclosed heretofore.

A well known process for producing 1-anthraquinonesulfonic acid, as is taught in Kirk-Othmer, "Encyclopedia of Chemical Technology", 3rd edition (1978), vol. 2, P.729, wherein anthraquinone is sulfonated in oleum in the presence of mercury salt, requires that the sulfonation reaction is interrupted as soon as about 45% of the starting anthraquinone have been converted, since otherwise disulfonation will be predominant.

U.S. Pat. No. 3,763,191 teaches a process for producing α-anthraquinonesulfonic acids in substantially higher yield and higher selectivity, especially if palladium or compounds containing the same are used. However, the degree of sulfonation and α-selectivity shown in the examples of said U.S. patent are still less than desired and furthermore, a process for recovering the catalyst solubilized in the reaction mixture is not disclosed therein.

U.S. Pat. No. 3,792,065 discloses a process for the production of α-anthraquinonesulfonic acids which are substantially devoid of mercury, in which mercury introduced in the form of the sulfate as the catalyst is seperated from the sulfonation mixture as metal by the addition of a reducing agent.

New catalysts which promote selectively the α-sulfonation of anthraquinone in liquid sulfur dioxide as a solvent are taught addressed in, "Palladium-Catalyzed α-Monosulfonation of Anthraquinone by Sulfur Trioxide in Liquid Sulfur Dioxide" by Yasuziro Kawabata, et al., appearing in Journal of the Chemical Society of Japan, 1980, (3), p. 322–326, wherein the use of liquid sulfur dioxide and palladium containing compounds in the sulfonation reaction resulted in about 100% conversion of anthraquinone and 76% yield of 1-anthraquinonesulfonic acid with 99% α-selectivity. Further, Kawabata, et al. disclose a process of reprecipitation of the solubilized palladium on carbon by hydrogen treating, in which the pH value of the reaction mixture was adjusted to >7, and then 20 atm hydrogen was introduced to deposit the solubilized Pd on carbon. However, the conversion of anthraquinone was found to have decreased to 70% as the recovered Pd-carbon was recycled. Additionally, air or oxygen was introduced into the mixture after the Pd-carbon had been removed in order to precipitate a salt of the monoanthraquinonesulfonic acid.

SUMMARY OF THE INVENTION

The present invention is a process for producing α-anthraquinonesulfonic acids, which comprises sulfonating anthraquinone in oleum in the presence of a metal catalyst which is deposited on a porous carrier; treating the resulting sulfonation mixture with a reducing agent such that the solubilized metal catalyst is redeposited on the porous carrier; and filtering out the catalyst and subsequently isolating α-anthraquinonesulfonic acid product from the mixture.

The high conversion ratio and high α-selectivity of the above sulfonation reaction together with the catalyst recovered retaining substantially the same activity afford a process for producing α-anthraquinonesulfonic acids more economical than any known process.

DETAILED DESCRIPTION OF THE INVENTION

The present invention provides a process for producing α-anthraquinonesulfonic acid products, especially 1-anthraquinonesulfonic acid, and for recovering the solubilized catalyst from the sulfonation mixture. The process involves sulfonating anthraquinone in oleum in the presence of a metal catalyst and reprecipitating the solubilized metal catalyst on an added porous carrier with a reducing agent.

In general, the metal catalysts which are disclosed in U.S. Pat. No. 3,763,191 the disclosure of which is incorporated herein by reference are suitable for use in the process. A group of suitable catalysts include ruthenium, rhodium, palladium, osmium, iridium, platinum, silver, gold, cobalt, nickel, mercury, thallium, and compounds containing the same. The preferred catalysts of the present invention are palladium, ruthenium, and compounds containing these metals, especially palladium and compound containing palladium, such as Pd, PdO, Pd(OAc)$_2$ et al. In the most preferred embodiment, sponge Pd particles having a mesh number greater than 60 are utilized as a starting catalyst.

Suitable materials for the porous carrier in the process are, for example, SiO$_2$, TiO$_2$, BaSO$_4$, anthraquinone, and carbon, wherein carbon is most preferable.

Oleum which has a SO$_3$ concentration higher than 20% may be used in the present process to decrease the amount of sulfuric acid in the resulting sulfonation mixture. Preferable SO$_3$ concentration of the oleum ranges from 35–45wt %. Further, the preferred mole ratio or SO$_3$ to anthraquinone is about 4:1.

As it is well known to those skilled in the art, the variables affecting the sulfonation reaction, such as reaction temperature, catalyst concentration, reaction time, will generally be controlled in accordance with the desired product. In one of the preferred embodiments of present invention, wherein palladium is used as catalyst and 1-anthraquinonesulfonic acid product is desired, the sulfonation reaction is accomplished at a temperature ranging from room temperature to 120° C., preferably ranging from 80° to 110° C., and a concentration of palladium catalyst ranging from 0.3–2.0wt %, based on anthraquinone, preferably ranging from 0.35–1.5wt %, and the reaction is stopped when at about 97% of the starting anthraquinone which has been converted to optimize the yield of the 1-anthraquinonesulfonic acid product The interruption of sulfonation reaction is effected by the addition of ice water or water, which also causes the reaction mixture to be diluted as well.

In general, reducing agents disclosed in U.S. Pat. No. 3,792,065 are suitable for use in the present process, and details thereof are incorporated by reference. The reducing agents, for example, include formaldehyde, glucose, sodium sulfite, potassium sulfite, sodium hydrogen sulfite, potassium hydrogen sulfite, sulfur dioxide, formic acid, sodium formate, potassium formate, oxalic acid, and neutral or alkali metal salts of oxalic acid, wherein formaldehyde is preferred.

The reducing reaction of solubilized metal catalyst according to the present invention may be carried out at atmospheric pressure with stirring at a temperature ranging from room temperature to 115° C., preferably ranging from 80° to 110° C. Particularly, adjusting the pH value of sulfonation mixture before reprecipitating the solubilized metal catalyst as taught by Kawabata et al. is not necessary for the present process The precipitated metal-carrier which is filtered out from the reaction mixture is washed with water until free from acid, and then dried to yield a catalyst which is ready to be used in the next sulfonation reaction. The 1-anthraquinonsulfonic acid product is obtained from the filtrate by the conventional salting out method.

The invention will be further illustrated by the following examples in which parts and precentages are by weight unless otherwise indicated.

EXAMPLE 1

The objectives of this example are to produce 1-anthraquinonesulfonic acid using sponge Pd particles as catalyst and to recover the sponge Pd catalyst as a deposited form.

0.83 g., mesh number 325, sponge Pd particles is introduced with stirring into 95 ml. of 25% oleum in a 500 ml. three-neck flask equipped with a mechanical agitator, a thermometer, and a heating jacket, the mixture is heated, and antraquinone whose weight is 125.5 times that of the Pd is added at 70° C., i.e. 104.2 g. anthraquinone is added, and 90 ml. of 65% oleum is dripped in slowly at 90° C. The temperature of the mixture reaches about 98° C. within 5–10 minutes and is maintained for 5 hours after the dripping began, and then a sample is taken from the mixture to find about 3.4% of the starting anthraquinone unreacted. The mixture heating is stopped and the mixture is left to cool to room temperature, and then it is introduced into 1100 ml. ice water, the flask reactor is washed with 100 ml water; and the washing water is combined with the diluted mixture. 17 g. active carbon and 75 g. of 37% formalin are added to the diluted aqueous solution and, the solution is heated and kept at about 110° C. for 45 minutes. When the solution is still hot, it is filtered to yield a cake of Pd-carbon. The cake is washed with 100 ml hot water to dissolve the undesired soluble material, filtered again, and dried to product the Pd-carbon catalyst which is used in the next sulfonation reaction in the following example. A sample taken from the mixture of the filtrate and the washing water is analyzed by AA method to measure the concentration of solubilized Pd.

The mixture of the filtrate and the washing water is heated to about 85° C., and saturated KCl aqueous solution is added. A total of KCl added is about and the mixture is kept at 85° C. with stirring for about 1 hour, and then heating is stopped and the mixture left to stand overnight. The potassium salt of 1-anthraquinonesulfonic acid is filtered out from above said mixture, the resulting cake is washed with 200 ml. of 3% KCl aqueous solution and dried. The potassium salt of 1-anthraquinone acid obtained from above process is 133.5 g., which is 85% based on converted anthraquinone.

The analytic data of the composition of the sulfonated product, and the loss of Pd are given in the following Table 1.

EXAMPLE 2

The objective of this example is to illustrate that the catalyst which is recovered according to the process of present invention will have substantially the same activity as the original catalyst.

The process of example 1 is repeated except that the sponge Pd particles are replaced by the Pd-carbon recovered from above example 1, designated as Pd-C(I), and the active carbon is not added into the reaction mixture before the reducing reaction The process is repeated for another two cycles using the Pd-carbon which is recovered from the previous process, designated as Pd-C(II) and Pd-C(III), respectively.

The analytic data of the composition of the sulfonated product, and the loss of Pd are given in the following Table 1.

TABLE 1

| Catalyst | Composition of Sulfonated Product (%)[b] | | | | Percentages[c] of Recovered Pd |
|---|---|---|---|---|---|
| | 1-AQ-SO₃H | 1.5— | 1.8— | Unidentified Material | |
| Pd.[a] | 85 | 2.3 | 3.6 | 9.1 | 100 |
| Pd-C(I) | 85 | 3.8 | 3.7 | 7.5 | 97.2 |
| Pd-C(II) | 85.4 | 3.8 | 3.5 | 7.3 | 94.2 |
| Pd-C(III) | 84.8 | 3.6 | 3.6 | 8.0 | 92.4 |

[a]Example 1.
[b]Data of the composition of sulfonated products obtained by HPLC method.
[c]Percentages of recovered Pd = [(weight of the starting Pd) − (weight of the solubilized Pd)]/(weight of the starting Pd) × 100%

As it can be seen from Table 1 the Pd-carbon recovered from each cycle has substantially the same activity as the starting sponge Pd particles, and further the loss of solubilized Pd is minimized to significant extent compared to the method taught Kawabata et al. In fact, the process of example 2 has been carried out as far as to the eleventh cycle, wherein the Pd-carbon recovered therefrom retains substantially the same activity as fresh sponge Pd particles.

What I claim as my invention is:

1. A process for producing α-anthraquinonesulfonic acids and recovering the catalyst used therein, which comprises:
   (a) sulfonating anthraquinone in oleum in the presence of a metal catalyst;
   (b) depositing the solubilized metal of the catalyst on a porous carrier by treating the resulting sulfonation mixture without adjusting the pH to a value greater than 7 with a reducing agent in the presence of said porous carrier;
   (c) separating the metal catalyst deposited on said porous carrier from the thus treated mixture; and subsequently
   (d) recovering the α-anthraquinonesulfonic acid product from the mixture.

2. A process in accordance with claim 1, wherein an additional quantity of anthraquinone is sulfonated in oleum employing the separated metal on said carrier as catalyst and the sulfonation mixture thus formed, without adjusting the pH to a value greater than 7, is treated with a reducing agent to precipitate solubilized metal.

3. A process in accordance with claim 2, wherein the sulfonation reaction in the step a is interrupted at a desired conversion degree of said anthraquinone by the addition of ice water or water.

4. A process in accordance with claim 2, wherein said metal catalyst is selected from the group consisting of palladium, ruthenium or compounds containing these metals.

5. A process in accordance with claim 4, wherein said metal is palladium.

6. A process in accordance with claim 5, wherein said metal catalyst is sponge palladium particles.

7. A process in accordance with claim 6, wherein said sponge palladium particles have a mesh number greater than 60.

8. A process in accordance with claim 1, wherein the sulfonation reaction in the step a is interrupted at a desired conversion degree of said anthraquinone by the addition of ice water or water.

9. A process in accordance with claim 1, wherein said α-anthraquinonesulfonic acid is 1-anthraquinonesulfonic acid.

10. A process in accordance with claim 1, wherein said metal is palladium or ruthenium.

11. A process in accordance with claim 10, wherein said metal is palladium.

12. A process in accordance with claim 1, wherein said reducing agent is selected from the group consisting of formaldehyde, glucose, sodium sulfite, potassium sulfite, sodium hydrogen sulfite, potassium hydrogen sulfite, sulfur dioxide, formic acid, sodium formate, potassium formate, oxalic acid, and neutral or alkali metal salts of oxalic acid.

13. A process in accordance with claim 12, wherein said reducing agent is formaldehyde.

14. A process in accordance with claim 13, wherein said metal catalyst contains palladium.

15. A process in accordance with claim 14, wherein the ratio of palladium to formaldehyde is from 1:25 to 1:50.

16. A process in accordance with claim 1, wherein the reducing position in said step b is carried out at a temperature ranging from 20°–120° C.

17. A process in accordance with claim 16, wherein the reducing reaction in said step b is carried out at a temperature ranging from 80°–100° C.

* * * * *